(12) United States Patent
Reich et al.

(10) Patent No.: US 7,872,118 B2
(45) Date of Patent: Jan. 18, 2011

US007872118B2

(54) SIRNA AND METHODS OF MANUFACTURE

(75) Inventors: Samuel Jotham Reich, Miami Beach, FL (US); N. Nicole Endejann, Streetsboro, OH (US)

(73) Assignee: Opko Ophthalmics, LLC, Miami, FL (US)

( * ) Notice: Subject to any disclaimer, the term of this patent is extended or adjusted under 35 U.S.C. 154(b) by 106 days.

(21) Appl. No.: 11/851,145

(22) Filed: Sep. 6, 2007

(65) Prior Publication Data

US 2009/0061487 A1 Mar. 5, 2009

Related U.S. Application Data

(60) Provisional application No. 60/824,953, filed on Sep. 8, 2006.

(51) Int. Cl.
C07H 21/04 (2006.01)
C07H 21/02 (2006.01)
C07H 21/00 (2006.01)
C12P 19/34 (2006.01)

(52) U.S. Cl. .................... 536/24.5; 435/91.1; 536/23.1; 536/25.3

(58) Field of Classification Search .................... None
See application file for complete search history.

(56) References Cited

U.S. PATENT DOCUMENTS

| | | | |
|---|---|---|---|
| 4,235,871 A | 11/1980 | Papahadjopoulos | |
| 4,501,728 A | 2/1985 | Geho et al. | |
| 4,837,028 A | 6/1989 | Allen | |
| 4,920,016 A | 4/1990 | Allen et al. | |
| 5,019,369 A | 5/1991 | Presant et al. | |
| 5,139,941 A | 8/1992 | Muzyczka et al. | |
| 5,252,479 A | 10/1993 | Srivastava | |
| 5,624,803 A | 4/1997 | Noonberg et al. | |
| 5,801,156 A | 9/1998 | Robinson et al. | |
| 5,902,598 A | 5/1999 | Chen et al. | |
| 6,015,894 A | 1/2000 | Bennett et al. | |
| 6,020,462 A | 2/2000 | Semenza | |
| 6,121,000 A | 9/2000 | Wright et al. | |
| 6,177,401 B1 | 1/2001 | Ullrich et al. | |
| 6,331,313 B1 | 12/2001 | Wong et al. | |
| 6,355,271 B1 | 3/2002 | Bell et al. | |
| 6,375,972 B1 | 4/2002 | Guo et al. | |
| 6,506,559 B1 | 1/2003 | Fire et al. | |
| 7,148,342 B2 | 12/2006 | Tolentino et al. | |
| 2002/0086356 A1 | 7/2002 | Tuschl et al. | |
| 2002/0132788 A1 | 9/2002 | Lewis et al. | |
| 2002/0162126 A1 | 10/2002 | Beach et al. | |
| 2002/0173478 A1 | 11/2002 | Gewirtz | |
| 2003/0138407 A1 | 7/2003 | Lu et al. | |
| 2003/0153519 A1 | 8/2003 | Kay et al. | |
| 2003/0216335 A1 | 11/2003 | Lockridge et al. | |
| 2004/0018176 A1 | 1/2004 | Tolentino et al. | |
| 2004/0096848 A1 | 5/2004 | Thrue et al. | |
| 2004/0115640 A1 | 6/2004 | Myers et al. | |
| 2004/0180357 A1 | 9/2004 | Reich et al. | |
| 2004/0220129 A1 | 11/2004 | Reich et al. | |
| 2004/0248174 A1 | 12/2004 | Reich et al. | |
| 2004/0259247 A1 | 12/2004 | Tuschl et al. | |
| 2005/0048529 A1 | 3/2005 | McSwiggen | |
| 2005/0159380 A1 | 7/2005 | Guerciolini et al. | |
| 2005/0187174 A1 | 8/2005 | Richards et al. | |
| 2005/0197315 A1 | 9/2005 | Taira et al. | |
| 2005/0246794 A1 | 11/2005 | Khvorova et al. | |
| 2007/0178068 A1 | 8/2007 | Reich et al. | |

FOREIGN PATENT DOCUMENTS

| | | |
|---|---|---|
| CA | 2359180 | 8/2000 |
| EP | 1144623 B1 | 8/2002 |
| WO | WO 93/24641 | 12/1993 |
| WO | WO 94/13788 | 6/1994 |
| WO | WO 01/57206 A2 | 8/2001 |
| WO | WO 01/75164 | 10/2001 |
| WO | WO 02/44321 | 6/2002 |
| WO | WO 02/096927 | 12/2002 |
| WO | WO 03/066805 A2 | 8/2003 |
| WO | WO 03/070910 | 8/2003 |
| WO | WO 03/087367 A2 | 10/2003 |
| WO | WO 03/087368 A2 | 10/2003 |
| WO | WO 03/099298 | 12/2003 |
| WO | WO 2004/009769 A2 | 1/2004 |
| WO | WO 2004/013310 A2 | 2/2004 |
| WO | WO 2004/065546 | 8/2004 |
| WO | WO 2004/094606 A2 | 11/2004 |
| WO | WO 2005/028649 A1 | 3/2005 |

OTHER PUBLICATIONS

Banan et al., The Ins and Outs of RNAi in Mammalian Cells, 2004, Current Pharmaceutical Biotechnology, 5, pp. 441-450.*
Bullard et al., Direct comparison of nick-joining activity of the nucleic acid ligases from bacteriophage T4, 2006, Biochem. Soc. 398:135-144.
Database retrieved from EBI accession No. GSN:ADY90830, [Online] Jun. 16, 2005, VEGF siRNA SEQ ID No. 3867, XP002468090.
Database retrieved from EBI accession No. GSN:ADY90830, [Online] Jun. 16, 2005, VEGF siRNA SEQ ID No. 3868, XP002468091.
Nandakumar et al., RNA Substrate Specificity and Structure-guided Mutational Analysis of Bacteriophage T4 RNA Ligase 2, 2004, J. Biol. Chem. 279(30):31337-31347.
Reich et al., Small interfering RNA (siRNA) targeting VEGF effectively inhibits ocular neovascularization in a mouse model, 2003, Molecular Vision 9:210-216.

(Continued)

*Primary Examiner*—Amy Bowman
(74) *Attorney, Agent, or Firm*—Pepper Hamilton LLP

(57) ABSTRACT

Double-stranded RNA of about 19 to about 25 nucleotides in length capable of regulating gene expression by RNA interference is provided. Such double-stranded RNA are particularly useful for treating disease or conditions associated with a target mRNA or gene. Methods of manufacture and methods of use of the double-stranded RNA are also provided.

12 Claims, 1 Drawing Sheet

OTHER PUBLICATIONS

Kurschat et al., Optimizing splinted ligation of highly structured small RNAs, 2005, Cold Spring Harbor Laboratory Press, 2005, pp. 1909-1914.

Harborth et al., Sequence, Chemical, and Structural Variation of Small Interfering RNAs and Short Hairpin RNAs and the Effect on Mammalian Gene Silencing, 2003, Antisense and Nucl. Acid Drug Dev. 13:83-105.

Elbashir et al., Functional anatomy of siRNAs for mediating efficient RNAi in Drosophila melanogaster embryo lysate, 2001, The EMBO J. 20(23):6877-6888.

Dorsett et al., siRNAs: Applications in Functional Genomics and Potential as Therepeutics, 2004, Nature 3(4):318-329.

Manoharan, RNA interference and chemically modified small interfering RNAs, 2004, Curr. Opin. Chem. Biol. 8:570-579.

Bustin, Absolute Quantification of mRNA using real-time reverse transcription polymerase chain reaction assays, 2000, J. Mol. Endocrinol. 25(2):169-193.

Tuschl et al., The siRNA User Guide, May 6, 2004, www.mpibpc.gwdg.de/abteilungen/100/105/sirna.html.

Tuschl, Expanding small RNA interference, 2002, Nat. Biotechnol. 20:446-448.

Brummelkamp et al., A System for Stable Expression of Short Interfering RNAs in Mammalian Cells, 2002, Science 296:550-553.

Miyagishi et al., U6 promoter-driven siRNAs with four uridine 3' overhangs efficiently suppress targeted gene expression in mammalian cells, 2002, Nat. Biotechnol. 19:497-500.

Paddison et al., Short hairpin RNAs (siRNAs) induce sequence-specific silencing in mammalian cells, 2002, Genes Dev. 16:948-958.

Lee et al., Expression of small interfering RNAs targeted against HIV-1 rev transcripts in human cells, 2002, Nat. Biotechnol. 19:500-505.

Paul et al., Effective expression of small interfering RNA in human cells, 2002, Nat. Biotechnol. 20:505-508.

Dornburg, Reticuloendotheliosis viruses and derived vectors, 1995, Gene Therap. 2:301-310.

Eglitis et al., Retroviral Vectors for Introduction of Genes into Mammalian Cells, 1988, Biotechniques 6(7):608-614.

Miller, Retrovirus Packaging Cells, 1990, Hum. Gene Therap. 1:5-14.

Anderson, Human Gene Therapy, 1998, Nature 392:25-30.

Xia et al., siRNA-mediated gene silencing in vitro and in vivo, 2002, Nat. Biotech. 20:1006-1010.

Samulski et al., A Recombinant Plasmid from Which an Infectious Adeno-Associated Virus Genome Can Be Excised In Vitro and Its Use to Study Viral Replication, 1987, J. Virol. 61(10):3096-3101.

Fisher et al., Transduction with Recombinant Adeno-Associated Virus for Gene Therapy is Limited by Leading-Strand Synthesis, 1996, J. Virol. 70(1):520-532.

Samulski et al., Helper-Free Stocks of Recombinant Adeno-Associated Viruses: Normal Integration Does Not Require Viral Gene Expression, 1989, J. Virol. 63(9):3822-3828.

Szoka, JR et al., Comparative Properties and Methods of Preparation of Lipid Vesicles (Liposomes), 1980, Ann. Rev. Biophys. Bioeng. 9:467-508.

Gabizon et al., Liposome formulations with prolonged circulation time in blood and enhanced uptake by tumors, 1988, P.N.A.S. USA 85:6949-6953.

Acheampong et al., Distribution of Brimonidine into Anterior and Posterior Tissues of Monkey, Rabbit, and Rat Eyes, 2002, Drug Metabol. and Disposition 30(4):421-429.

Bennett et al., Humoral response after administration of E1-deleted adenoviruses: immune privilege of the subretinal space, 1996, Hum. Gene Ther. 7:1763-1769 (Abstract).

Ambati et al., Transscleral drug delivery to the retina and choroid, 2002, Progress in Retinal and Eye Res. 21:145-151.

Remington's Pharmaceutical Sciences, 17$^{th}$ ed. Mack Publishing Co., Easton, PA, 1985.

Fire et al., Potent and specific genetic interference by double-stranded RNA in Caenorhabditis elegans, 1998, Nature 391:806-811.

Elbashir et al., RNA interference is mediated by 21-and 22-nucleotide RNAs, 2001, Genes Dev. 15:188-200.

Elbashir et al., Duplexes of 21-nucleotide RNAs mediate RNA interference in cultured mammalian cells, 2001, Nature 411:494-498.

McCaffrey et al., RNA interference in adult mice, 2002, Nature 418:38-39.

Novina et al., siRNA-directed inhibition of HIV-1 infection, 2002, Nat. Med. 8(7):681-686.

Belletti et al., Modulation of in vivo growth of thyroid tumor-derived cell lines by sense and antisense vascular endothelial growth factor gene, 1999, Oncogene 18:4860-4869.

Roberts et al., Efficient expression of ribozyme and reduction of stromelysin mRNA in cultured cells and tissue from rabbit knee via Adeno-associated Virus (AAV), 1999, Gene Therapy and Molecular Biology 4:45-58.

Rubinson et al., Nature Genetics, Published online Feb. 18, 2003, doi:10.1308/ng1117, vol. 33(3):401-406 (Abstract).

Shu et al., Sphingosine Kinase Mediates Vascular Endothelial Growth Factor-Induced Activation of Ras and Mitogen-Activated Protein Kinases, 2002, Mol. Cell Biol. 22(22):7758-7768.

Holash et al., VEGF-Trap: A VEGF blocker with potent antitumor effects, 2002, PNAS USA 99(17):11393-11398.

Kim et al., Potent VEGF blockade causes regression of coopted vessels in a model of neuroblastoma, 2002, PNAS USA 99(17):11399-11404.

Tischer et al., The human gene for vascular endothelial growth factor. Multiple protein forms are encoded through alternative exon splicing, Jun. 25, 1991, J. Biol. Chem. 266(18):11947-11954 (Abstract).

Erickson, RNAi Revs Up, Oct. 2002, Start-Up, RNAi Revs Up (A#2002900168) pp. 1-12.

Nishiwaki et al., Introduction of short interfering RNA to silence endogenous E-selection in vascular endothelium leads to successful inhibition of leukocyte adhesion, 2003, Biochem. Biophys. Res. Commun. 310(4):1062-1066.

Warren et al., Successful ICAM-1 Gene Inactivation in Pluripotent Stem Cell Using RNA Interference and in Situ Expressed Antisense/Ribozyme Transgenes, 2002, J. Am. Soc. Nephrology, p. 101A (Abstract).

Devroe et al., Retrovirus-delivered siRNA, 2002, BMC Biotechnology, Biomed Central Ltd., London, GB, pp. 1-5.

Kretschmer-Kazemi Far et al., The activity of siRNA in mammalian cells is related to structural target accessibility: a comparison with antisense oligonucleotides, 2003, Nucl. Acids Res. 31(15):4417-4424.

Vickers et al., Efficient Reduction of Target RNAs by Small Interfering RNA and RNase H-dependent Antisense Agents, 2003, J. Biol. Chem. 278(9):7108-7118.

Miyamoto et al., Vascular endothelial growth factor (VEGF)-Induced Retinal Vascular Permeability is mediated by Intercellular Adhesion Molecule-1 (ICAM-1), 2000, Am. J. Pathology 156(5):1733-1739.

Miyamoto et al., Prevention of Leukostasis and vascular leakage in streptozotocin-induced diabetic retinopathy via intercellular adhesion molecule-1 inhibition, 1999, Proc. Nathl. Acad. Sci. USA 96:10836-10841.

Moromizato et al., CD18 and ICAM-1 Dependent Corneal Neovascularization and Inflammation after Limbal Injury, 2000, Am. J. Pathology 157(4):1277-1281.

Sakurai et al., Targeted disruption of the CD18 or ICAM-1 gene inhibits choroidal neovascularization, 2003, Invest. Ophthalmol. Vis. Sci. 44(6):2743-2749.

Katz et al., ICAM-1 Antisense Oligodeoxynucleotide Improves Islet Allograft Survival and Function, 2000, Cell Trans. 9:817-828.

Dragun et al., ICAM-1 antisense oligodeoxynucleotides prevent reperfusion injury and enhance immediate graft function in renal transplantation, 1998, Kidney Inter. 54:590-602.

Agrawal et al. Antisense therapeutics: is it as simple as complementary base recognition?, 2000, Mol. Med. Today 6:72-81.

Jen et al., Suppression of Gene Expression by Targeted Disruption of Messenger RNA: Available Options and Current Strategies, 2000, Stem Cells 18:307-319.

Coburn et al., siRNAs: a new wave of RNA-based therapeutics, 2003, Antimicrobial Chemotherapy 51:753-756.

Agami, RNAi and related mechanisms and their potential use for therapy, 2002, Curr. Op. Chem. Biol. 6:829-834.

Downward et al., Science, medicine and the future, RNA interference, 2004, BMJ 328:1245-1248.

Paroo et al., Challenges for RNAi in vivo, 2004, Trends in Biotechnology 22:390-394.

Lu et al., Delivering siRNA in vivo for functional genomics and novel therapeutics. From RNA Interference Technology. 2005, Cambridge, Appasani et al., pp. 303-317.

Samarsky et al., RNAi in drug development, Practical Considerations. From RNA interference Technology, 2005, Cambridge, Appasani et al., pp. 384-395.

Fjose et al., RNAi and MicroRNAs: from Animal Models to Disease Therapy, 2006, Birth Defects Research 78:150-171.

Kang et al., An Antisense Oligonucleotide that Inhibits the Expression of Hypoxia-Inducible Factor-1 alpha Alters Hypoxia-Induced Changes in Proliferation and viability of Human Cardiac Fibroblasts, 57:11 (Abstract).

Sun et al., Gene Transfer of Antisense Hypoxia Inducible Factor-1 alpha Enhances the therapeutic Efficacy of Cancer Immunotherapy, 2001, Gene Therapy 8:638-645.

Brantl, Antisense-RNA regulation and RNA interference, 2002, Biochimica et Biophys. Acta 1575:15-25.

Zheng et al., Protection of Renal Ischemia Injury using Combination Gene Silencing of Complement 3 and Caspase 3 Genes, 2006, Transplantation 82(12):1781-1786.

Songsivilai et al., Bispecific antibody: a tool for diagnosis and treatment of disease, 1990, Clin. Exp. Immunol. 79:315-321.

Kostelny et al., Formation of a bispecific antibody by the use of leucine zippers, 1992, J. Immunol. 148(5):1547-1553.

Stein et al., Oligodeoxynucleotides as Inhibitors of Gene Expression: A Review, 1988, Cancer Res. 48:2659-2668.

Van Der Krol et al., Modulation of eukaryotic gene expression by complementary RNA or DNA sequences 1988, BioTechniques 6(10):958-976.

Ostergaard, et al., Complement activation and diabetic vascular complications, Apr. 2005, Clinica Chimica Acta, pp. 1-10.

Engstrom et al., Complement C3 is a Risk Factor for the Development of Diabetes: A Population-Based Cohort Study, Feb. 2005, Diabetes 54:570-575.

Fujita et al., Complement Activation Accelerates Glomerular Injury in Diabetic Rats, Aug. 1998, Nephron 81:208-214.

Kock et al., Structure and Function of Recombinant Cobra Venom Factor, 2004, J. Biol. Chem. 279(29):30836-30843.

Ganesh et al., Structure of vaccinia complement protein in complex with heparin and potential implications for complement regulation, 2004, PNAS 101(24):8924-8929.

Sun et al., Prolonged cardiac xenograft survival in guinea pig-to-rat model by a highly active cobra venom factor, 2003, Toxicon 42:257-262.

Hodgetts et al., Complement and myoblast transfer therapy: Donor myoblast survival is enhanced following depletion of host complement C3 using cobra venom factor, but not in the absence of C5, 2001, Immunol. and Cell Biol. 79:231-239.

Andra et al., Generation and characterization of transgenic mice expressing cobra venom factor, 2002, Mol. Immun. 39:357-365.

Shen et al., A Study of Cobra Venom Factor in Ex Vivo Pig Liver Perfusion Model, 2001, Transplantation Proc. 33:3860-3861.

Vogel et al., Recombinant cobra venom factor, 2004, Molecular Immun. 41:191-199.

Chen et al., Prevention of Hyperacute Rejection of Pig-to-Monkey Cardiac Xenografts by Chinese Cobra Venom Factor, 2001, Transplantation Proc. 33:3857-3858.

Bora et al., Role of Complement and Complement Membrane Attack Complex in Laser-Induced Choroidal Neovascularization, 2005, J. Immun. 174:491-497.

Sohn et al., Complement Regulatory Activity of Normal Human Intraocular Fluid is Mediated by MCP, DAF and CD59, 2000, Invest. Ophthal. & Vis. Sci. 41(13):4195-4202.

Sohn et al., Tolerance is dependent on complement C3 fragment iC3b binding to antigen-presenting cells, 2003, Nature Med. 9(2):206-212.

Daiger, Was the Human Genome Project Worth the Effort?, 2005, Science 308:362-364.

Kuehn, Gene Discovery Provides Clues to Cause of Age-Related Macular Degeneration, 2005, JAMA 293(15):1841, 1845.

Bok, Evidence for an inflammatory process in age-related macular degeneration gains new support, 2005, PNAS 102(20):7053-7054.

Conley et al., Candidate gene analysis suggests a role for fatty acid biosynthesis and regulation of the complement system in the etiology of age-related maculopathy, 2005, Human Mol. Genetics 14(14):1991-2002.

Edwards et al., Complement Factor H Polymorphism and Age-Related Macular Degeneration, 2005, Science 308:421-424.

Hageman et al., A common haplotype in the complement regulatory gene factor H (HF1/CFH) predisposes individuals to age-related macular degeneration, 2005, PNAS 102(20):7227-7232.

Haines et al., Complement Factor H Variant Increases the Risk of Age-Related Macular Degeneration, 2005, Science 308:419-421.

Jakobsdottir et al., Susceptibility Genes for Age-Related Maculopathy on Chromosome 10q26, 2005, Am. J. Hum. Genet. 77:389-407.

Klein et al., Complement Factor H Polymorphism in Age-Related Macular Degeneration, 2005, Science 308:385-389.

Zareparsi et al., Strong Association of the Y402H Variant in Complement Factor H at 1q32 with Susceptibility to Age-Related Macular Degeneration, 2005, Am J. Human Genet. 77:149-153.

Russell et al., Location, Substructure, and Composition of Basal Laminar Drusen Compared with Drusen Associated with Aging and Age-Related Macular Degeneration, 2000, Am. J. Ophthalmology 129(2):205-214.

Johnson et al., A Potential Role for Immune Complex Pathogenesis in Drusen Formation, 2000, Exp. Eye Res. 70:441-449.

Johnson et al., Complement Activation and Inflammatory Processes in Drusen Formation and Age Related Macular Degeneration, 2001, Exp. Eye Res. 73:887-896.

Anderson et al., A Role for Local Inflammation in the Formation of Drusen in the Aging Eye, 2002, Am. J. Ophth. 134(3):411-431.

Anderson et al., Vitronectin Gene Expression in the Adult Human Retina, 1999, Invest. Ophth. & Vis. Sci. 40(13):3305-3315.

Mullins et al., Drusen associates with aging and age-related macular degeneration contain proteins common to extracellular deposits associated with atherosclerosis, elastosis, amyloidosis, and dense deposit disease, 2000, FASEB J. 14:835-846.

Hageman et al., An Integrated Hypothesis that Considers Drusen as Biomarkers of Immune-Mediated Processes at the RPE-Bruch's Membrane Interface in Aging and Age-Related Macular Degeneration, 2001, Progress in Ret. & Eye Res. 20(6):705-732.

Johnson et al., The Alzheimer's Aβ-peptide is deposited at sites of complement activation in pathologic deposits associated with aging and age-related macular degeneration, 2002, PNAS 99(18):11830-11835.

Hageman et al., Molecular composition of drusen as related to substructural phenotype, 1999, Molecular Vision 5:28-37.

Walport, Complement, First of Two Parts, 2001, N. Eng. J. Med. 344(14):1058-1066.

Walport, Complement at the Interface Between Innate and Adaptive Immunity, 2001, N. Eng. J. Med. , Complement: Second of Two Parts, 344(15):1140-1144.

Mastellos et al., Novel biological networks modulated buy complement, 2005, Clinical Immunol. 115:225-235.

Linton et al., Therapeutic-efficacy of a novel membrane-targeted complement regulator in antigen-induced arthritis in the rat, 2000, Arthritis Rheum. 43(11):2590-2597 (Abstract).

Mollnes et al., Complement in inflammatory tissue damage and disease, 2002, TRENDS in Immunol. 23(2):61-64.

Pratt et al., Nontransgenic Hyperexpression of a Complement Regulator in Donor Kidney Modulates Transplant Ischemia/Reperfusion Damage, Acute Rejection, and Chronic Nephropathy, 2003, Am. J. Pathology 163(4):1457-1465.

Jha et al., Vaccinia complement control protein: Multi-functional protein and a potential wonder drug, 2003, J. Biosci. 28(3):265-271.

Lucas et al. Secreted Immunomodulatory Viral Proteins as Novel Biotherapeutics, 2004, J. Immunol. 173:4765-4774.

Holers et al., The alternative pathway of complement in disease: opportunities for therapeutic targeting, 2004, Mol. Immunol. 41:147-152.

Finehout et al., Complement protein isoforms in CSF as possible biomarkers for neurodegenerative disease, 2005, Dis Markers 21(2):93-101 (Abstract).

Speidl et al., Complement component C5a predicts future cardiovascular events in patients with advanced atherosclerosis, 2005, Eur. Heart J. 26:2294-2299.

Ohali et al., Complement profile in childhood immune thrombocytopenic purpura: a prospective pilot study, 2005, Ann. Hematol. 84(12):812-815.

Dyer et al., The role of complement in immunological demyelination of the mammalian spinal cord, 2005, Spinal Cord 43(7):417-425.

Guo et al., Role of C5A in Inflammatory Responses, 2005, Annu. Rev. Immunol. 23:821-852.

Xu et al., Protective effect of membrane cofactor protein against complement-dependent injury, 2005, Acta Pharmacologica Sinica 8:987-991.

Peng et al., Role of C5 in the development of airway inflammation, airway hyperresponsiveness, and ongoing airway response, 2005, J. Clin. Investigation 115(6):1590-1600.

Fung et al., Inhibition of complement, neutrophil, and platelet activation by an anti-factor D monoclonal antibody in simulated cardiopulmonary bypass circuits, 2001, J. Thoracic and Cardiovascular Surgery 122(1):113-122.

Halstead et al., Complement Inhibition Abrogates Terminal Injury in Miller Fisher Syndrome, 2005, Ann. Neurol. 58:203-210.

Hart et al., Initiation of complement activation following oxidative stress. In vitro and in vivo observations, 2004, Molecular Immunology 41:165-171.

Nuckel et al., Alemtuzumab induces enhanced apoptosis in vitro in B-cells from patients with chromic lymphocytic leukemia by antibody-dependent cellular cytotoxicity, 2005, Eur. J. Pharmacology 514(2-3):217-224.

Ames et al., Identification of a Selective Nonpeptide Antagonist of the Anaphylatoxin C3a Receptor That Demonstrates Antiinflammatory Activity in Animal Models, 2001, J. Immunol. 166:6341-6348.

Smith et al., Membrane-targeted complement inhibitors, 2001, Molecular Immunology 38:249-255.

Gompels et al., C1 inhibitor deficiency: consensus document, 2005, Clinical and Experimental Immunol. 139:379-394.

Mastellos et al., From atoms to systems: a cross-disciplinary approach to complement-mediated functions, 2004, Molecular Immunol. 41:153-164.

Rother et al., Inhibition of terminal complement: a novel therapeutic approach for the treatment of systemic lupus erythematosus, 2004, Lupus 13:328-334.

Blom et al., Complement inhibitor C4b-binding protein-friend or foe in the innate immune system?, 2004, Molecular Immunol. 40:1333-1346.

Strachan et al., A New Small Molecule C5a Receptor Antagonist Inhibits the Reverse-Passive Arthus Reaction and Endotoxic Shock in Rats, 2000, J. Immunol. 164:6560-6565.

Sewell et al., Complement C3 and C5 play critical roles in traumatic brain cryoinjury: blocking effects on neutrophil extravasation by C5a receptor antagonist, 2004, J. Neuroimmunol. 155:55-63.

Bao et al., C5a promotes development of experimental lupus nephritis which can be blocked with a specific receptor antagonist, 2005, Eur. J. Immunol. 35(8):2496-2506.

Cai et al., A Direct Role for C1 Inhibitor in Regulation of Leukocyte Adhesion, 2005, J. Immunol. 174:6462-6466.

Thurman et al., A novel inhibitor of the alternative complement pathway prevents antiphospholipid antibody-induced pregnancy loss in mice, 2005, Molecular Immunol. 42:87-97.

He et al., Complement Inhibitors Targeted to the Proximal Tubule Prevent Injury in Experimental Nephrotic Syndrome and demonstrate a Key role for C5b-9, 2005, J. Immunol. 174:5750-5757.

Addis-Lieser et al., Opposing Regulatory Roles of Complement Factor 5 in the Development of Bleomycin-Induced Pulmonary Fibrosis, 2005, J. Immunol. 175:1894-1902.

Hillebrandt et al., Complement factor 5 is a quantitative trait gene that modifies liver fibrogenesis in mice and humans, 2005, Nat. Genetics 37:835-843.

Shim et al., Inhibition of Angiopoietin-1 Expression in Tumor Cells by an Antisense RNA Approach Inhibited Xenograft Tumor Growth in Immunodeficient Mice, 2001, Int. J. Canc 94:6-15.

Hammond et al., Post-Transcriptional Gene Silencing by Double-Stranded RNA, 2001, Nature Reviews: Genetics 2:110-119.

Schroder et al., A single-stranded promoter for RNA polymerase III, 2003, PNAS 100(3):934-939.

Ward et al., Genomic structure of the human angiopoietins show polymorphism in angiopoietin-2, 2001, Cytogenetic and Genome Res. 94:147-154.

Bass et al., The Short Answer, 2001, Nature 41:428-429, MacMillan Magazines Ltd.

Bartz et al., Production of High-Titer Human Immunodeficiency Virus type 1 Pseudotyped with vesicular stomatitis virus glycoprotein, 1997, Enzymology 12:237-342, Academic Press.

Tuschl, The siRNA User Guide (revised Oct. 11, 2002), www.mpibpc.gwdg.de/abteilungen/100/105/sirna.html.

GenBank Accession No. AF214570 (Apr. 25, 2007).

Van Brunt, Shoot the Messenger, Signals Magazine (Aug. 22, 2002), www.signalsmag.com/signalsmag ..../3DF5AEF6049C88256C1D0055BAA.

Caplen, RNAi as a gene therapy approach, *Expert Opin. Biol. Ther.* (2003), 3(4):575-586.

Hoeg, et al., In vitro and in vivo efficacy of a HIF-1alpha-antisense oligonucleotide containing locked nucleic acids, *ECJ Supplements* (Sep. 24, 2003), pp. S212-S213.

Krishnamachary, et al., Regulation of Colon Carcinoma Cell Invasion by Hypoxia-Inducible Factor 1 [1], *Cancer Research* (Mar. 1, 2003), 63:1138-1143.

Alexion Pharmaceuticals, News & Information, Alexion Pharmaceuticals Initiates Treatment in Pivotal Phase III Eculizumab Program in Paraxysmal Nocturnal Hemoglobinuria Patients (Sep. 23, 2004), www.alexionpharm com.

Sohn, et al., Chronic Low Level Complement Activation within the Eye is Controlled by Intraocular Complement Regulatory Proteins, *IOVS.* (Oct. 2000), 41(11):3492-3502.

* cited by examiner

SEQUENCE LISTING

<160> NUMBER OF SEQ ID NOS: 11

<210> SEQ ID NO 1
<211> LENGTH: 19
<212> TYPE: DNA
<213> ORGANISM: Homo sapiens

<400> SEQUENCE: 1
tcatcacgaa gtggtgaag                                              19

<210> SEQ ID NO 2
<211> LENGTH: 21
<212> TYPE: RNA
<213> ORGANISM: Homo sapiens

<400> SEQUENCE: 2
ucaucacgaa guggugaagu u                                           21

<210> SEQ ID NO 3
<211> LENGTH: 21
<212> TYPE: RNA
<213> ORGANISM: Homo sapiens

<400> SEQUENCE: 3
uuaguagugc uucaccacuu c                                           21

```
<210> SEQ ID NO 4
<211> LENGTH: 21
<212> TYPE: DNA
<213> ORGANISM: Homo sapiens
<220> FEATURE:
<223> OTHER INFORMATION: Antisense strand
<220> FEATURE:
<221> NAME/KEY: misc_feature
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 4
ucaucacgaa guggugaagt t                                              21

<210> SEQ ID NO 5
<211> LENGTH: 21
<212> TYPE: DNA
<213> ORGANISM: Homo sapiens
<220> FEATURE:
<223> OTHER INFORMATION: Sense strand
<220> FEATURE:
<221> NAME/KEY: misc_feature
<222> LOCATION: (1)...(2)
<223> OTHER INFORMATION: deoxyribonucleotides
<220> FEATURE:
<221> NAME/KEY: misc_feature
<222> LOCATION: (3)...(21)
<223> OTHER INFORMATION: deoxyribonucleotides

<400> SEQUENCE: 5
ttaguagugc uucaccacuu c                                              21

<210> SEQ ID NO 6
<211> LENGTH: 21
<212> TYPE: DNA
<213> ORGANISM: Homo sapiens
<220> FEATURE:
<223> OTHER INFORMATION: Sense strand
<220> FEATURE:
<221> NAME/KEY: misc_feature
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 6
accucaccaa ggccagcact t                                              21

<210> SEQ ID NO 7
<211> LENGTH: 21
<212> TYPE: DNA
<213> ORGANISM: Homo sapiens
<220> FEATURE:
<223> OTHER INFORMATION: Antisense strand
<220> FEATURE:
<221> NAME/KEY: misc_feature
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 7
gugcuggccu uggugaggut t                                              21
```

```
<210> SEQ ID NO 8
<211> LENGTH: 21
<212> TYPE: DNA
<213> ORGANISM: Homo sapiens
<220> FEATURE:
<223> OTHER INFORMATION: Sense strand
<220> FEATURE:
<221> NAME/KEY: misc_feature
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 8
ggcuacgucc aggagcgcat t                                              21

<210> SEQ ID NO 9
<211> LENGTH: 21
<212> TYPE: DNA
<213> ORGANISM: Homo sapiens
<220> FEATURE:
<223> OTHER INFORMATION: Antisense strand
<220> FEATURE:
<221> NAME/KEY: misc_feature
<222> LOCATION: (1)...(19)
<223> OTHER INFORMATION: ribonucleotides
<220> FEATURE:
<221> NAME/KEY: misc_feature
<222> LOCATION: (20)...(21)
<223> OTHER INFORMATION: deoxyribonucleotides

<400> SEQUENCE: 9
ugcgcuccug gacguagcct t                                              21

<210> SEQ ID NO 10
<211> LENGTH: 10
<212> TYPE: RNA
<213> ORGANISM: Homo sapiens

<400> SEQUENCE: 10
accucaccaa                                                           10

<210> SEQ ID NO 11
<211> LENGTH: 11
<212> TYPE: DNA
<213> ORGANISM: Homo sapiens
<220> FEATURE:
<223> OTHER INFORMATION: Antisense strand
<220> FEATURE:
<221> NAME/KEY: misc_feature
<222> LOCATION: (1)...(9)
<223> OTHER INFORMATION: ribonucleotides
<220> FEATURE:
<221> NAME/KEY: misc_feature
<222> LOCATION: (10)...(11)
<223> OTHER INFORMATION: deoxyribonucleotides

<400> SEQUENCE: 11
ggccagcact t                                                         11
```

SIRNA AND METHODS OF MANUFACTURE

CROSS REFERENCE TO RELATED APPLICATION

This application claims priority to U.S. Application No. 60/824,953 filed Sep. 8, 2006 entitled "siRNA and Methods of Manufacture", herein incorporated by reference in its entirety.

GOVERNMENT INTERESTS

Not Applicable

PARTIES TO A JOINT RESEARCH AGREEMENT

Not Applicable

INCORPORATION BY REFERENCE OF MATERIAL SUBMITTED ON A COMPACT DISC

BACKGROUND OF THE INVENTION

Not Applicable
a. Field of Invention
Not Applicable
b. Description of Related Art
Not Applicable

SUMMARY OF THE INVENTION

One embodiment of the present invention provides methods of manufacturing isolated siRNA that may be useful as therapeutic agents. In certain embodiments, such methods may include the synthesis of two or more nucleotide strands. In further embodiments, the method may include the synthesis of three, four or more nucleotide sub-strands, wherein the total length of the sets of sub-strands is from about 19 to about 25 nucleotides in length.

In one embodiment, the method of preparing a double-stranded RNA molecule comprises synthesizing a first set of two or more RNA sub-strands, wherein the combined length of the first set of sub-strands is from about 19 to about 25 nucleotides, synthesizing a second set of two or more RNA sub-strands, wherein the combined length of the second set of sub-strands is from about 19 to about 25 nucleotides; and combining the synthesized first and second set of RNA sub-strands under conditions, wherein a double-stranded RNA molecule is formed which is at 19 to at 25 nucleotides in length, and further may have single stranded regions of about 1 to about 5 nucleotides at the 3' ends of at least one of the strands of the double-stranded RNA molecule.

In another embodiment, a method of preparing a double-stranded RNA molecule comprises synthesizing one RNA strand having a length from about 19 to about 25 nucleotides, (b) synthesizing a second RNA strand and a third RNA strand, wherein the combined length of the second RNA strand and the third RNA strand is from about 19 to about 25 nucleotides; and combining the synthesized RNA strands under conditions, wherein a double-stranded RNA molecule is formed, wherein the double-stranded RNA molecule consists of a single double stranded region and single stranded regions of about 1 to about 5 nucleotides at the 3' ends of at least one of the strands of the double-stranded RNA molecule.

In a further embodiment, a method of preparing a double-stranded RNA molecule comprises synthesizing a first set of two or more RNA sub-strands, wherein the combined length of the first set of sub-strands is 25 or fewer nucleotides, synthesizing a second set of two or more RNA sub-strands, wherein the combined length of the second set of sub-strands is 25 or fewer nucleotides; and combining the synthesized first and second set of RNA sub-strands under conditions, wherein a double-stranded RNA molecule is formed.

In another embodiment, a method of preparing a double-stranded RNA molecule comprises synthesizing one RNA strand having a length from 25 or fewer nucleotides, synthesizing a second RNA strand and a third RNA strand, wherein the combined length of the second RNA strand and the third RNA strand is 25 or fewer nucleotides; and combining the synthesized RNA strands under conditions, wherein a double-stranded RNA molecule is formed, wherein the double-stranded RNA molecule consists of a single double stranded region and single stranded regions of about 1 to about 5 nucleotides at the 3' ends of at least one of the strands of the double-stranded RNA molecule.

BRIEF DESCRIPTION OF THE DRAWINGS

For a fuller understanding of the nature and advantages of the present invention, reference should be had to the following detailed description taken in connection with the accompanying drawings, in which.

DETAILED DESCRIPTION OF THE INVENTION

Figure 1:
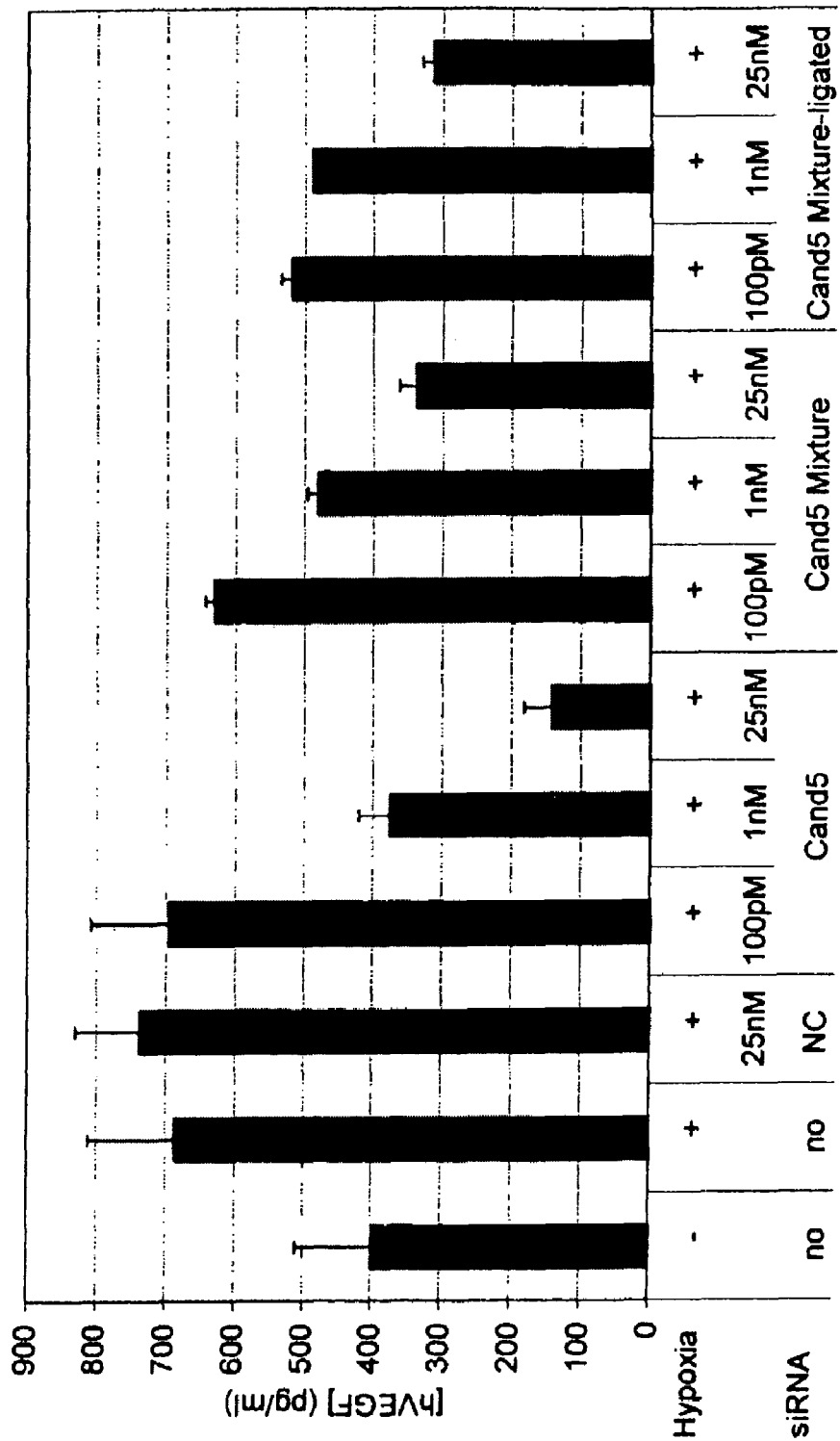
FIG. 1 is a bar graph comparing the efficacy of a specific siRNA targeting VEGF prepared by synthesizing and combining two strands of RNA (Cand5) and a specific siRNA targeting VEGF prepared by synthesizing and combining three strands of RNA without ligase (Cand5 mixture) or with ligase (Cand 5 mixture-ligated) 293 cells at various concentrations.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "molecule" is a reference to one or more molecules and equivalents thereof known to those skilled in the art, and so forth. As used herein, the term "about" means plus or minus 10% of the numerical value of the number with which it is being used. Therefore, about 50% means in the range of 45%-55%.

Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA to within one nucleotide resolution. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Synthetic siRNA of 21 and 22 nucleotides in length, and which have short 3' overhangs, are able to induce RNAi of target mRNA in a Drosophila cell lysate. Cultured mammalian cells also exhibit RNAi degradation with synthetic siRNA, and RNAi degradation induced by synthetic siRNA has recently been shown in living mice. The therapeutic potential of siRNA-induced RNAi degradation has been demonstrated in several recent in vitro studies, including the siRNA-directed inhibition of HIV-1 infection and reduction of neurotoxic polyglutamine disease protein expression. siRNA-directed inhibition of VEGF has also been demonstrated as set forth in U.S. Pat. No. 7,148,342, filed Nov. 4, 2002, herein incorporated by reference in its entirety.

One aspect of the present invention provides isolated siRNA comprising short double-stranded RNA from about 17 nucleotides to about 29 nucleotides in length, preferably from about 19 to about 25 nucleotides in length, that are targeted to a given mRNA. The siRNA comprise a sense RNA strand and a complementary antisense RNA strand annealed together by standard Watson-Crick base-pairing interactions (hereinafter "base-paired"). In one embodiment, as is described in more detail below, the sense strand comprises a nucleic acid sequence which is identical to a target sequence contained within the target mRNA. In a further embodiment, the sequence of the double-stranded RNA molecule of the present invention has to have a sufficient identity to a nucleic acid target molecule in order to mediate target-specific RNAi and/or DNA methylation. Preferably, the sequence has an identity of at least 50%, particularly of at least 70% to the desired target molecule in the double-stranded portion of the RNA molecule. More preferably, the identity is a least 85% and most preferably 100% in the double-stranded portion of the RNA molecule. The identity of a double-stranded RNA molecule to a predetermined nucleic acid target molecule, e.g. an mRNA target molecule may be determined as follows:

$$I = \frac{n}{L} \times 100$$

wherein I is the identity in percent, n is the number of identical nucleotides in the double-stranded portion of the dsRNA and the target and L is the length of the sequence overlap of the double-stranded portion of the dsRNA and the target. Alternatively, the identity of the double-stranded RNA molecule to the target sequence may also be defined including the 3' overhand, particularly an overhang having a length from 1-3 nucleotides. In this case the sequence identity is preferably at least 50%, more preferably at least 70% and most preferably at least 85% to the target sequence, For example, the nucleotides from the 3' overhang and up to 2 nucleotides from the 5' and/or 3' terminus of the double strand may be modified without significant loss of activity.

The sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

The target gene to which the RNA molecule of the invention is directed may be associated with a pathological condition. For example, the gene may be a pathogen-associated gene, e.g. a viral gene, a tumor-associated gene or an autoimmune disease-associated gene. The target gene may also be a heterologous gene expressed in a recombinant cell or a genetically altered organism. By determining or modulating, particularly, inhibiting the function of such a gene valuable information and therapeutic benefits in the agricultural field or in the medicine or veterinary medicine field may be obtained. In a preferred embodiment, the target gene selected from VEGF (see U.S. Pat. No. 7,148,342, herein incorporated by reference in its entirety), HIF-1α (see U.S. Publication No. 20040180357 (Ser. No. 10/699,557) herein incorporated by reference in its entirety), ICAM-1 (see U.S. Publication No. 20040220129 (Ser. No. 10/759,878), herein incorporated by reference in its entirety), Angiopoietin 1, Angiopoietin 2 and Tie 2 (see U.S. Publication No, 20040248174 (Ser. No. 10/827,759), herein incorporated by reference in its entirety) and complement, including C3 (see U.S. application Ser. No. 11/615,554, herein incorporated by reference in its entirety).

Genes can be analyzed for further alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), *J. Mol. Endocrinol.* 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the target genes can be used to query such a database to determine whether ESTs representing alternatively spliced mRNAs have been found for a these genes.

A technique called "RNAse protection" can also be used to identify alternatively spliced mRNAs. RNAse protection involves translation of a gene sequence into synthetic RNA, which is hybridized to RNA derived from other cells; for example, cells from tissue at or near the site of neovascularization. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced mRNAs. In RT-PCR, mRNA from the diseased tissue is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

mRNA produced from mutant genes can also be readily identified through the techniques described above for identifying alternative splice forms. As used herein, "mutant" genes or mRNA include genes or mRNA which differ in sequence from the known sequences. Thus, allelic forms of these genes, and the mRNA produced from them, are considered "mutants" for purposes of this invention.

It is understood that a given mRNA may contain target sequences in common with their respective alternative splice forms, cognates or mutants. A single siRNA comprising such a common targeting sequence can therefore induce RNAi-mediated degradation of different RNA types which contain the common targeting sequence.

The siRNA can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA can also comprise a 3' overhang. As used herein, a "3' overhang" refers to at least one unpaired nucleotide extending from the 3'-end of a duplexed RNA strand.

Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, or from about 1 to about 3 nucleotides in length and particularly preferably from about 2 to about 4 nucleotides in length, and more preferably about 2 nucleotides in length.

In the embodiment in which both strands of the siRNA molecule comprise a 3' overhang, the length of the overhangs can be the same or different for each strand. In a most preferred embodiment, the 3, overhang is present on both strands of the siRNA, and is 2 nucleotides in length. For example, each strand of the siRNA of the invention can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, for example 2'-deoxythymidine is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the siRNA comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is convened to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the siRNA comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

The siRNA can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon (see, e.g., the target sequences of SEQ ID NOS: 73 and 74 in Table 1 below, which are within 100 nt of the 5'-end of the $VEGF_{121}$ cDNA).

For example, a suitable target sequence in the $VEGF_{121}$ cDNA sequence is:

```
    TCATCACGAAGTGGTGAAG       (SEQ ID NO: 1)
```

Thus, an siRNA of the invention targeting this sequence, and which has 3' uu overhangs on each strand (overhangs shown in bold), is:

```
    5'-ucaucacgaaguggugaaguu-3'    (SEQ ID NO: 2)

3'-uuaguagugcuucaccacuuc-5'    (SEQ ID NO: 3)
```

An siRNA of the invention targeting this same sequence, but having 3' TT overhangs on each strand (overhangs shown in bold) is:

```
5'-ucaucacgaaguggugaagTT-3'    (SEQ ID NO: 4)

3'-TTaguagugcuucaccacuuc-5'    (SEQ ID NO: 5)
```

Preferably, the siRNA are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

In one embodiment, the double-stranded RNA molecule may be prepared by synthesizing two RNA strands each having a length from about 19 to about 25, e.g. from about 19 to about 23, nucleotides, wherein said RNA strands are capable of forming a double-stranded RNA molecule, wherein preferably at least one strand has a 3'-overhang from 1-5 nucleotides, and combining the synthesized RNA strands under conditions, where a double-stranded RNA molecule is formed, which is capable of mediating target-specific nucleic acid modifications, particularly RNA interference and/or DNA methylation.

In another embodiment the double-stranded RNA molecule may be prepared by synthesizing multiple RNA strands and combining the multiple strands under conditions where a double-stranded RNA molecule is formed that is capable of mediating target-specific nucleic acid modifications, particularly RNA interference and/or DNA methylation. In one embodiment, three RNA strands may be synthesized, wherein one RNA strand has a length from about 19 to about 25 nucleotides and the second RNA strand, a first sub-strand, has a length from about 1 to about 24 nucleotides and the third RNA strand, a second sub-strand, has a length from about 1 to about 24 nucleotides, such that when the RNA sub-strands are combined they have a total length of about 19 to about 25 nucleotides in length. For example, one RNA strand may have a length from about 19 nucleotides, a first RNA sub-strand may have a length of two nucleotides and a second RNA sub-strand may have a length of about 17 nucleotides. In a further example, one RNA strand may have a length from about 19 nucleotides, a second RNA strand may have a length of 3 nucleotides and a third RNA strand may have a length of about 16 nucleotides.

In one preferred embodiment, the double-stranded RNA molecule may be prepared by synthesizing three RNA strands, each of a different length, for example, one RNA strand has a length of about 21 nucleotides, a second RNA strand has a length of about 10 nucleotides and a third RNA strand has a length of about 11 nucleotides. The three synthesized RNA strands are combined under conditions where a double-stranded RNA molecule is formed that has a 2 nucleotide overhang on the 3' ends of each RNA strand. In an additional embodiment, a ligase may be added to ligate the two RNA strands of the shortest length.

In another embodiment, the double-stranded RNA molecule may be prepared by synthesizing multiple RNA sub-strands and combining the multiple strands under conditions where a double-stranded RNA molecule is formed that is capable of mediating target-specific nucleic acid modifications, particularly RNA interference and/or DNA methylation. For example, four or more RNA sub-strands may be synthesized and combined to form a double-stranded molecule that is capable of RNA interference, wherein the total length of each of the two strands, after combining the sub-strands, that make up the double-stranded molecule has a length of about 19 to about 25 nucleotides.

In one embodiment, the method of preparing a double-stranded RNA molecule comprises synthesizing a first set of two or more RNA sub-strands, wherein the combined length of the first set of sub-strands is from about 19 to about 25 nucleotides, synthesizing a second set of two or more RNA sub-strands, wherein the combined length of the second set of sub-strands is from about 19 to about 25 nucleotides; and combining the synthesized first and second set of RNA sub-strands under conditions, wherein a double-stranded RNA molecule is formed.

In a further embodiment, a method of preparing a double-stranded RNA molecule comprises synthesizing one RNA strand having a length from about 19 to about 25 nucleotides, synthesizing a second RNA strand and a third RNA strand, wherein the combined length of the second RNA strand and the third RNA strand is from about 19 to about 25 nucleotides; combining the synthesized RNA strands under conditions, wherein a double-stranded RNA molecule is formed, wherein the double-stranded RNA molecule consists of a single double stranded region and single stranded regions of about 1 to about 5 nucleotides at the 3' ends of at least one of the strands of the double-stranded RNA molecule.

One embodiment comprises synthesizing a first set of two or more RNA sub-strands, wherein the combined length of the first set of sub-strands is from about 19 to about 25 nucleotides, synthesizing a second set of two or more RNA sub-strands, wherein the combined length of the second set of sub-strands is from about 19 to about 25 nucleotides; and combining the synthesized first and second set of RNA sub-strands under conditions, wherein a double-stranded RNA molecule is formed.

In one embodiment, the method of preparing a double-stranded RNA molecule comprises synthesizing a first set of two or more RNA sub-strands, wherein the combined length of the first set of sub-strands is from about 19 to about 25 nucleotides, synthesizing a second set of two or more RNA sub-strands, wherein the combined length of the second set of sub-strands is from about 19 to about 25 nucleotides; and combining the synthesized first and second set of RNA sub-strands under conditions, wherein a double-stranded RNA molecule is formed.

In another embodiment, a method of preparing a double-stranded RNA molecule comprises synthesizing one RNA strand having a length from about 19 to about 25 nucleotides, (b) synthesizing a second RNA strand and a third RNA strand, wherein the combined length of the second RNA strand and the third RNA strand is from about 19 to about 25 nucleotides; and combining the synthesized RNA strands under conditions, wherein a double-stranded RNA molecule is formed, wherein the double-stranded RNA molecule consists of a single double stranded region and single stranded regions of about 1 to about 5 nucleotides at the 3' ends of at least one of the strands of the double-stranded RNA molecule.

In a further embodiment, a method of preparing a double-stranded RNA molecule comprises synthesizing a first set of two or more RNA sub-strands, wherein the combined length of the first set of sub-strands is 25 or fewer nucleotides, synthesizing a second set of two or more RNA sub-strands, wherein the combined length of the second set of sub-strands is 25 or fewer nucleotides; and combining the synthesized first and second set of RNA sub-strands under conditions, wherein a double-stranded RNA molecule is formed In another embodiment, a method of preparing a double-stranded RNA molecule comprises synthesizing one RNA strand having a length from 25 or fewer nucleotides, synthesizing a second RNA strand and a third RNA strand, wherein the combined length of the second RNA strand and the third RNA strand is 25 or fewer nucleotides; and combining the synthesized RNA strands under conditions, wherein a double-stranded RNA molecule is formed, wherein the double-stranded RNA molecule consists of a single double stranded region and single stranded regions of about 1 to about 5 nucleotides at the 3' ends of at least one of the strands of the double-stranded RNA molecule.

It is to be understood that in each of the foregoing embodiments, a sub-strand is at least 2 nucleotides in length, and may be 2, 3, 4, 5, 6, 7, 8, 9, 10, 11, 12, 13, 14, 15, 16, 17, 18, 19, 20, 21, 22, or 23 nucleotides in length.

In each of the foregoing methods, the RNA strands or sub-strands may be chemically or enzymatically synthesized. The double-stranded RNA molecule comprises a single double stranded region and single stranded regions of about 1 to about 5 nucleotides at the 3' ends of at least one or both of the strands of the double-stranded RNA molecule. For example, in preferred embodiments, both strands of the double-stranded RNA molecule each have a 3'-overhang from about 1 to about 3 nucleotides, preferably about 2 nucleotides. In each of the foregoing methods, each strand may have a length from 19 to about 25 nucleotides, preferably about 20-22 nucleotides.

The double-stranded RNA molecule may comprises at least one sugar-modified nucleotide, wherein the 2'-OH group of said sugar-modified nucleotide is replaced by a group selected from H, OR, R, halo. SH, SR, $NH_2$, NHR, $N(R)_2$ or CN, wherein R is $C_1$-$C_6$ alkyl, alkenyl or alkynyl and halo is F, C, Br or I. The double-stranded RNA molecule may comprise at least one backbone-modified nucleotide containing a phosphorothioate group.

In another embodiment, a method of preparing a double-stranded RNA molecule comprises selecting a target mammalian mRNA or target gene sequence, synthesizing a first RNA strand having a length from about 19 to about 25 nucleotides, wherein the first RNA strand is complementary to contiguous nucleotides in the target sequence, synthesizing a second RNA strand; synthesizing a third RNA strand, wherein the second and third RNA strands are complementary to about 16 to about 24 nucleotides from the first RNA strand; combining the synthesized RNA strands under conditions suitable to form a double stranded RNA molecule, wherein said double stranded RNA molecule consists of a single double stranded region of from about 16 to about 24 nucleotides in length and one or two single stranded 3' overhang regions of about 1 to about 3 nucleotides in length each.

Methods of synthesizing RNA molecules are known in the art. In this context, it is particularly referred to chemical synthesis methods as described in Verma and Eckstein (1998). The single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlembeck (1989)).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA of the invention to cells in vivo is discussed in more detail below.

siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art, See, for example Tuschl, T. (2002), *Nat. Biotechnol,* 20: 446-448; Brummelkamp T R et al. (2002), *Science* 296: 550-553; Miyagishi M et al. (2002), *Nat. Biotechnol.* 20: 497-500; Paddison P J et al. (2002), *Genes Dev.* 16: 948-958; Lee N S et al. (2002), *Nat. Biotechnol.* 20: 500-505; and Paul C P et al. (2002), *Nat. Biotechnol.* 20: 505-508, the entire disclosures of which are herein incorporated by reference.

A plasmid comprising nucleic acid sequences for expressing an siRNA of the invention is described in Example 7 below. That plasmid, called pAAVsiRNA, comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid pAAVsiRNA is ultimately intended for use in producing an recombinant adeno-associated viral vector comprising the same nucleic acid sequences for expressing an siRNA of the invention.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "sunder the control" of a promoter means that the nucleic acid sequences encoding the sense or antisense strands are located 3' of the promoter, so that the promoter can initiate transcription of the sense or antisense coding sequences.

The siRNA of the invention can also be expressed from recombinant viral vectors intracellularly at or near the area of neovascularization in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

siRNA of the invention can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

Preferred viral vectors are those derived from AV and AAV. In a particularly preferred embodiment, the siRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA of the invention, a method for constructing the recombinant AV vector, and a method for delivering the vector into target cells, are described in Xia H et al. (2002), *Nat. Biotech.* 20: 1006-1010.

Suitable AAV vectors for expressing the siRNA of the invention, methods for constructing the recombinant AAV vector, and methods for delivering the vectors into target cells are described in Samulski R et al. (1987), *J. Virol.* 61: 3096-3101; Fisher K J et al. (1996), *J. Virol.*, 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. An exemplary method for generating a recombinant AAV vector of the invention is described in Example 7 below.

The ability of an siRNA containing a given target sequence to cause RNAi-mediated degradation of the target mRNA can be evaluated using standard techniques for measuring the levels of RNA or protein in cells. For example, siRNA can be delivered to cultured cells, and the levels of target mRNA can be measured by Northern blot or dot blotting techniques, or by quantitative RT-PCR. Alternatively, the levels of the target mRNA or protein in the cultured cells can be measured by ELISA or Western blot. A suitable cell culture system for measuring the effect of the present siRNA on target mRNA or protein levels is described in Example 1 below.

RNAi-mediated degradation of target mRNA by an siRNA containing a given target sequence can also be evaluated with animal models. For example, areas of neovascularization in an ROP or CNV mouse can be measured before and after administration of an siRNA. A reduction in the areas of neovascularization in these models upon administration of the siRNA indicates the down-regulation of the target mRNA.

In one preferred embodiment, the siRNA target and cause the RNAi-mediated degradation of, for example, VEGF, Flt-1 or Flk-1/KDR mRNA, or alternative splice forms, mutants or cognates thereof, Degradation of the target mRNA by the present siRNA reduces the production of a functional gene product from the VEGF, Flt-1 or Flk-1/KDR genes. Thus, the invention provides a method of inhibiting expression of VEGF, Flt-1 or Flk-1/KDR in a subject, comprising administering an effective amount of an siRNA of the invention to the subject, such that the target mRNA is degraded. As the products of the VEGF, Flt-1 and Flk-1/KDR genes are required for initiating and maintaining angiogenesis, the invention also provides a method of inhibiting angiogenesis in a subject by the RNAi-mediated degradation of the target mRNA by the present siRNA.

In another preferred embodiment, siRNA target and cause the RNAi-mediated degradation of, for example, human HIF-1 alpha gene or alternative splice forms, mutants or cognates thereof. Degradation of the target mRNA by the present siRNA reduces the production of a functional gene product from the HIF-1 alpha gene. Thus, the invention provides a method of inhibiting expression of HIF-1 alpha in a subject, comprising administering an effective amount of an siRNA of the invention to the subject, such that the target mRNA is degraded. As the products of the HIF-1 alpha gene are required for initiating and maintaining angiogenesis, the invention also provides a method of inhibiting angiogenesis in a subject by the RNAi-mediated degradation of the target mRNA by the present siRNA.

In another preferred embodiment, siRNA target and cause the RNAi-mediated degradation of, for example, human ICAM-1 gene or alternative splice forms, mutants or cognates thereof. Degradation of the target mRNA by the present siRNA reduces the production of a functional gene product from the ICAM-1 gene. Thus, the invention provides a method of inhibiting expression of ICAM-1 in a subject, comprising administering an effective amount of an siRNA of the invention to the subject, such that the target mRNA is degraded. As the products of the ICAM-1 gene are required for initiating and maintaining angiogenesis, the invention also provides a method of inhibiting angiogenesis in a subject by the RNAi-mediated degradation of the target mRNA by the present siRNA.

In another preferred embodiment, siRNA target and cause the RNAi-mediated degradation of, for example, human Ang1, Ang2 or Tie2 gene or alternative splice forms, mutants or cognates thereof. Degradation of the target mRNA by the present siRNA reduces the production of a functional gene product from the Ang1, Ang2 or Tie2 genes. Thus, the invention provides a method of inhibiting expression of Ang1, Ang2 or Tie2 in a subject, comprising administering an effective amount of an siRNA of the invention to the subject, such that the target mRNA is degraded. As the products of the Ang1, Ang2 or Tie2 genes are required for initiating and maintaining angiogenesis, the invention also provides a method of inhibiting angiogenesis in a subject by the RNAi-mediated degradation of the target mRNA by the present siRNA.

In another preferred embodiment, siRNA target and cause the RNAi-mediated degradation of, for example, human complement genes or alternative splice forms, mutants or cognates thereof. Degradation of the target mRNA by the present siRNA reduces the production of a functional gene product from the complement genes. Thus, the invention provides a method of inhibiting expression of complement in a subject, comprising administering an effective amount of an siRNA of the invention to the subject, such that the target mRNA is degraded.

As used herein, a "subject" includes a human being or non-human animal. Preferably, the subject is a human being.

As used herein, an "effective amount" of the siRNA is an amount sufficient to cause RNAi-mediated degradation of the target mRNA, or an amount sufficient to inhibit the progression of angiogenesis in a subject.

RNAi-mediated degradation of the target mRNA can be detected by measuring levels of the target mRNA or protein in the cells of a subject, using standard techniques for isolating and quantifying mRNA or protein as described above.

It is understood that the siRNA of the invention can degrade the target mRNA in substoichiometric amounts. Without wishing to be bound by any theory, it is believed that the siRNA of the invention causes degradation of the target mRNA in a catalytic manner.

Generally, an effective amount of the siRNA of the invention comprises an intercellular concentration at or near the neovascularization site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

In one embodiment, an effective amount of the siPNA of the invention comprises about from about 0.1 mg to about 20 mg of siRNA. In a further embodiment, the effective amount is from about 0.2 mg to about 10 mg of siRNA. In an additional embodiment, preferably the effective amount of the siRNA is from about 0.5 to about 5 mg of siRNA. Further preferred embodiments provide effective amounts of about 1 mg to about 3 mg, including about 1.5 mg, 2.5 mg or about 3 mg of siRNA.

For treating diseases, the siRNA of the invention can administered to a subject in combination with a pharmaceutical agent which is different from the present siRNA. Alternatively, the siRNA of the invention can be administered to a subject in combination with another therapeutic method designed to treat the subject disease. For example, the siRNA of the invention can be administered in combination with therapeutic methods currently employed for treating cancer or preventing tumor metastasis (e.g., radiation therapy, chemotherapy, and surgery). For treating tumors, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

In certain embodiments, the siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as retinal or tumor tissue, and can also increase the blood half-life of the siRNA. Liposomes suitable for use are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., (1980), *Ann. Rev, Biophys. Bioeng.* 9: 467; and U.S. Pat. Nos. 4,235, 871, 4,501,728, 4,837,028, and 5,019,369, the entire disclosures of which are herein incorporated by reference.

Preferably, the liposomes encapsulating the present siRNA comprises a ligand molecule that can target the liposome to a particular cell or tissue at or near the site of therapeutic need. For example, ligands which bind to receptors prevalent in tumor or vascular endothelial cells, such as monoclonal antibodies that bind to tumor antigens or endothelial cell surface antigens, are preferred.

Particularly preferably, the liposomes encapsulating the siRNA are modified so as to avoid clearance by the mononuclear macrophage and reticuloendothelial systems, for example by having opsonization-inhibition moieties bound to the surface of the structure. In one embodiment a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), *P.N.A.S., USA,* 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids which express siRNA of the invention are discussed above. Such recombinant plasmids can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA of the invention are also discussed above, and methods for delivering such vectors to an area of neovascularization in a patient are within the skill in the art.

The siRNA of the invention can be administered to the subject by any means suitable for delivering the siRNA to the cells of the tissue at or near the area of neovascularization. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intravitreal injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation. Suitable placement devices include the ocular implants described in U.S. Pat. Nos. 5,902,598 and 6,375,972, and the biodegradable ocular implants described in U.S. Pat. No. 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.).

In a preferred embodiment, injections or infusions of the siRNA are given at or near the site of neovascularization. More preferably, the siRNA is administered topically to the eye, e.g. in liquid or gel form to the lower eye lid or conjunctival cul-de-sac, as is within the skill in the art (see, e.g., Acheampong A A et al, 2002, *Drug Metabol, and Disposition* 30: 421-429, the entire disclosure of which is herein incorporated by reference).

In such embodiments, the siRNA of the invention may be administered topically to the eye in amounts of from about 5 microliters to about 75 microliters, for example from about 7 microliters to about 50 microliters, preferably from about 10 microliters to about 30 microliters. It is understood that topical instillation in the eye of siRNA in volumes greater than 75 microliters can result in loss of siRNA from the eye through spillage and drainage. Thus, it is preferable to administer a high concentration of siRNA (e.g., 100-1000 nM) in as small a volume as possible.

A particularly preferred parenteral administration route is intraocular administration. It is understood that intraocular administration of the present siRNA can be accomplished by injection or direct (e.g., topical) administration to the eye, as long as the administration route allows the siRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong A A et al, 2002, supra; and Bennett et al. (1996), *Hum. Gene Ther.* 7: 1763-1769 and Ambati J et al., 2002, *Progress in Retinal and Eye Res.* 21: 145-151, the entire disclosures of which are herein incorporated by reference.

The siRNA of the invention can be administered in a single dose or in multiple doses. Where the administration of the siRNA of the invention is by infusion, the infusion can be a single sustained dose or can be delivered by multiple infusions. Injection of the agent directly into the tissue is at or near the site of neovascularization preferred. Multiple injections of the agent into the tissue at or near the site of neovascularization are particularly preferred.

The siRNA can be administered to the subject once, such as by a single injection or deposition at or near the neovascularization site. Alternatively, the siRNA can be administered to a subject multiple times daily or weekly. For example, the siRNA can be administered to a subject once weekly for a period of from about three to about twenty-eight weeks, more preferably from about seven to about ten weeks. In a preferred dosage regimen, the siRNA is injected at or near the site of neovascularization (e.g., intravitreally) once a week for seven weeks. It is understood that periodic administrations of the siRNA of the invention for an indefinite length of time may be necessary for subjects suffering from a chronic neovascularization disease, such as wet ARMD or diabetic retinopathy.

Where a dosage regimen comprises multiple administrations, it is understood that the effective amount of siRNA administered to the subject can comprise the total amount of siRNA administered over the entire dosage regimen.

The siRNA of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science,* 17th ed., Mack Publishing Company, Easton, Pa. (1985), the entire disclosure of which is herein incorporated by reference.

The present pharmaceutical formulations comprise an siRNA of the invention (e.g., 0.1 to 90% by weight), or a physiologically acceptable salt thereof, mixed with a physiologically acceptable carrier medium. Preferred physiologically acceptable carrier media are water, buffered water, saline solutions (e.g., normal saline or balanced saline solutions such as Hank's or Earle's balanced salt solutions), 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For topical administration to the eye, conventional intraocular delivery reagents can be used. For example, pharmaceutical compositions of the invention for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers. Preferably, the intraocular delivery reagent increases corneal penetration, or prolongs preocular retention of the siRNA through viscosity effects or by establishing physicochemical interactions with the mucin layer covering the corneal epithelium.

Suitable insoluble particles for topical intraocular delivery include the calcium phosphate particles described in U.S. Pat. No. 6,355,271 of Bell et al., the entire disclosure of which is herein incorporated by reference. Suitable polymers which undergo a viscosity increase upon instillation in the eye include polyethylenepolyoxypropylene block copolymers such as poloxamer 407 (e.g., at a concentration of 25%), cellulose acetophthalate (e.g., at a concentration of 30%), or a low-acetyl gellan gum such as Gelrite® (available from CP Kelco, Wilmington, Del.). Suitable mucoadhesive polymers include hydrocolloids with multiple hydrophilic functional groups such as carboxyl, hydroxyl, amide and/or sulfate groups, for example, hydroxypropylcellulose, polyacrylic acid, high-molecular weight polyethylene glycols (e.g. >200,000 number average molecular weight), dextrans, hyaluronic acid, polygalacturonic acid, and xylocan. Suitable corneal penetration enhancers include cyclodextrins, benzalkonium chloride, polyoxyethylene glycol lauryl ether (e.g., Brij® 35), polyoxyethylene glycol stearyl ether (e.g., Brij® 78), polyoxyethylene glycol oleyl ether (e.g., Brij® 98), ethylene diamine tetraacetic acid (EDTA), digitonin, sodium taurocholate, saponins and polyoxyethylated castor oil such as Cremaphor EL.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA of the invention. A pharmaceutical composition for aerosol (inhalational) administration can comprise 0.01-20% by weight, preferably 1%-10% by weight, of one or more siRNA of the invention encapsulated in a liposome as described above, and propellant. A carrier can also be included as desired; e.g., lecithin for intranasal delivery.

EXAMPLE 1

Two different methods of producing siRNA were evaluated and the efficacy of the resulting siRNA were tested. Specifically, Cand5 duplex was formed by each of the methods and the resulting products were tested for their ability to inhibit VEGF in human embryonic kidney 293 cells.

Three different RNA single-stranded oligonucleotides were prepared. These included a 10 base pair (bp) oligonucleotides encoding bp 1-10 of the Cand5 sense strand, an 11 bp oligonucleotides encoding bp 11-21 of the Cand5 sense strand; and an oligonucleotides encoding the entire Cand5 antisense strand. In the first method, the oligonucleotides were combined in an equimolar ratio, heated to 95° C. for 2 minutes and then cooled to room temperature. In the second method, the oligonucleotides were also combined and heated as described; however, T4 DNA ligase was added to the mixture post-cooling, and the sample was incubated at room temperature for an hour and then at 65° C. for 15 minutes.

The ability of each method's resulting product to reduce VEGF protein levels in cell culture was evaluated. Human embryonic kidney 293 cells were transiently transfected with each of the products. Hypoxia was induced in the cells with the addition of desferrioxamine in order to induce VEGF transcription and translation. Forty-eight hours post-transfection, media was collected and an ELISA was performed to quantify the levels of secreted VEGF protein. Both synthesis methods allowed for the formation of the Cand5 duplex, and the resulting Cand5 caused a dose-dependent decrease in VEGF protein.

Cell Culture. Human embryonic kidney 293 cells (ATCC, Manassas, Va.) were cultured in Dulbecco's Modified Eagle Medium (DMEM; Cellgro, Herndon, Va.) with 10% fetal bovine serum (FBS; JRH Biosciences, Lenexa, Kans.) and an antibiotic-antimycotic reagent used for the prevention of cell culture growth contaminants (Gibco. Carlsbad, Calif.) under 5% $CO_2$ at 37° C.

siRNAs and Oligonucleotides. All siRNAs and oligonucleotides were synthesized by Dharmacon (Lafayette, Colo.). The fully synthesized Cand5 siRNA served as a positive control in the in vitro efficacy studies. The sense strand sequence was 5'-ACC UCA CCA AGG CCA GCA CdTdT-3' (SEQ ID NO. 6), while the antisense strand sequence was 5'-G UGC UGG CCU UGG UGA GGUdTdT-3' (SEQ ID NO. 7).

An siRNA targeting enhanced green fluorescent protein (EGFP) served as a negative control. The sense strand sequence for this siRNA was 5'-GGC UAC GUC CAG GAG CGC AdTdT-3' (SEQ ID NO. 8), and the antisense strand sequence was 5'-U GCG CUC CUG GAC GUA GCCdTdT-3, (SEQ ID NO. 9).

Three different single-strand RNA oligonucleotides were synthesized: one encoding base pairs 1-10 of the Cand5 sense strand 5'-ACC UCA CCA A-3' (SEQ ID NO. 10); one encoding base pairs 11-21 of the Cand5 sense strand 5'-GG CCA GCA CdTdT-3' (SEQ ID NO. 11); and one encoding the Cand5 antisense strand 5'-G UGC UGG CCU UGC UGA GGUdTdT-3' (SEQ ID NO 7).

Combining the Cand5 RNA Precursor Oligonucleotides. Each of the three RNA oligonucleotides were combined in equimolar amounts. They were then mixed, heated to 95° C. for 2 minutes, and allowed to cool down to room temperature. The resulting "Cand5 Mixture" was either used for in vitro studies directly (see below) or further modified to facilitate ligation of the sense strand components prior to use. The additional modification involved combing 10 μL of the "Cand5 Mixture" with 0.5 μL of T4 ligase (5 U/μl, Ambion, Austin, Tex.), 1.5 μL 10× ligation buffer and 3 μL of water. The sample was incubated at room temperature for one hour and then incubated at 65° C. for an additional 15 minutes to inactivate the ligase. The resulting product was termed "Cand5 Mixture-ligated".

siRNA Transfection and Hypoxia Induction in Vitro. 293 cells were cultured in 24-well plates at 37° C. with 5% $CO_2$ and incubated overnight. After approximately 24 hours of incubation, when the cells were estimated to be 70% confluent, aliquots of Cand5 Mixture or Cand5 Mixture-ligated were added, along with a calcium phosphate (CaPi) reagent. Cand5 duplex, "Cand5 Mixture", or "Cand5 Mixture-ligated" was added to 20 μL of 250 mM CaCl$_2$ solution. The siRNA/CaCl$_2$ mixture was added drop-wise to 20 μL of 2× Hanks Balanced Salt Solution (HBS), while mixing by vortex. The siRNA/CaCl$_2$/HBS complex was added directly to the medium (300 μL/well). After 4 hours of incubation at 37° C., the medium was removed, and the cells were further incubated with 10% DMSO-containing serum-free medium (300 μL/well at room temperature for 1-2 minutes). This medium was then removed, and the cells were fed again with 500 μmL/well growth medium. The final concentration of siRNA dilutions were 100 pM, 1 nM, and 25 nM. Negative controls included the transfection reagent lacking siRNA or the nonspecific siRNA (EGFP siRNA) at a 25 nM concentration. To stimulate VEGF transcription and translation within the cells, hypoxia was induced with the addition of desferrioxamine (Sigma, Saint Louis, Mo.) at a final concentration of 130 μM, which was introduced to the cultures 4 hours after transfection was performed. The assay was performed on duplicate plates with samples prepared in triplicate.

VEGF Protein Quantification. Approximately 48 hours post-transfection, the cell supernatant was removed from each well for analysis. The Quantikine human VEGF ELISA Kit (R&D Systems, Minneapolis, Minn.) was used to quantify VEGF protein, following the manufacturer's protocol. 100 μL of each sample were analyzed. The ELISA results were read at 450 nm using an AD340 plate reader (Beckman-Coulter).

Results and Discussion. Human VEGF protein was upregulated in 293 cells treated with desferrioxamine, as shown in FIG. 1. The hypoxia-induced increase in hVEGF protein was significantly reduced in cells treated with Cand5 (Dharmacon), "Cand5 Mixture" and "Cand5 Mixture-ligated". The effect was dose-dependent. Treatment with non-specific siRNA (EGFP siRNA; 25 nM NC), or mock incubations without siRNA, had no effect on hVEGF levels. Cand5 showed better suppression than "Cand5 Mixture" and "Cand5 Mixture-ligated".

Both methods involved the synthesizes and combination of the three RNA oligonucleotides, collectively encoding the sense and antisense strands of Cand5, in equimolar ratios, however, the methods contemplated by the present invention may involve the synthesis and combination of multiple oligonucleotides in non-equimolar ratios. In one method described above, the oligonucleotides were joined by mixing, heating to 95° C. and cooling to room temperature, In the other method described above, the ligation of the sense strand components was facilitated by the subsequent addition of ligase to the mixture.

Both methods allowed for Cand5 duplex formation, which is evident by the mixtures' abilities to suppress human VEGF protein production in hypoxic 293 cells; however, neither mixture appeared to be as effective as the Cand5 duplex. This is likely due to the fact that products from the two methods were not enriched for the Cand5 duplex. In addition, there was similar efficacy between the mixture without ligase and that with ligase, suggesting that addition of ligase does not contribute to duplex formation.

Although the present invention has been described in considerable detail with reference to certain preferred embodiments thereof other versions are possible. Therefore the spirit and scope of the appended claims should not be limited to the description and the preferred versions contained within this specification.

What is claimed is:

1. A method of preparing a double-stranded RNA molecule comprising
    (a) synthesizing one RNA strand having a length from about 19 to about 25 nucleotides,
    (b) synthesizing a second RNA strand and a third RNA strand, wherein the combined length of the second RNA strand and the third RNA strand is from about 19 to about 25 nucleotides;
    (c) combining the synthesized RNA strands under conditions, wherein a double-stranded RNA molecule is formed, wherein the double-stranded RNA molecule consists of a single double stranded region and single stranded regions of about 1 to about 5 nucleotides at the 3' ends of at least one of the strands of the double-stranded RNA molecule.

2. The method according to claim 1, wherein the RNA strands are chemically synthesized.

3. The method according to claim 1, wherein the RNA strands are enzymatically synthesized.

4. The method of claim 1, wherein the double-stranded RNA molecule comprises a single double stranded region and single stranded regions of about 1 to about 5 nucleotides at the 3' ends of at least one of the strands of the double-stranded RNA molecule.

5. The method of claim 1, wherein both strands of the double-stranded RNA molecule each have a 3'-overhang from about 1 to about 5 nucleotides.

6. The method of claim 1, wherein both strands of the double-stranded RNA molecule each have a 3'-overhang of about 2 nucleotides.

7. The method of claim 1, wherein the one RNA strand has a length from about 20 to about 22 nucleotides and the combined length of the second RNA strand and the third RNA strand is from about 20 to about 22 nucleotides.

8. The method of claim 1, wherein the double-stranded RNA molecule comprises at least one sugar-modified nucleotide, wherein the 2'—OH group of said sugar-modified nucleotide is replaced by a group selected from H, OR, R, halo, SH, SR, $NH_2$, NHR, $N(R)_2$ or CN, wherein R is $C_1$-$C_6$ alkyl, alkenyl or alkynyl and halo is F, Cl, Br or I.

9. The method of claim 1, wherein the double stranded RNA molecule comprises at least one backbone-modified nucleotide containing a phosphorothioate group.

10. A method of preparing a double-stranded RNA molecule comprising
    (a) synthesizing one RNA strand having a length from 25 or fewer nucleotides,
    (b) synthesizing a second RNA strand and a third RNA strand, wherein the combined length of the second RNA strand and the third RNA strand is 25 or fewer nucleotides;
    (c) combining the synthesized RNA strands under conditions, wherein a double-stranded RNA molecule is formed, wherein the double-stranded RNA molecule consists of a single double stranded region and single stranded regions of about 1 to about 5 nucleotides at the 3' ends of at least one of the strands of the double-stranded RNA molecule.

11. The method of claim 10, wherein the double-stranded RNA molecule comprises a single double stranded region and single stranded regions of about 1 to about 5 nucleotides at the 3' ends of at least one of the strands of the double-stranded RNA molecule.

12. The method of claim 10, wherein the one RNA strand has a length from 20-22 nucleotides and the combined length of the second RNA strand and the third RNA strand is from 20-22 nucleotides.

\* \* \* \* \*